United States Patent [19]

Schwender et al.

[11] 4,076,710

[45] Feb. 28, 1978

[54] BENZO[g]PYRIDO[2,1-b]-QUINAZOLI-NONES

[75] Inventors: Charles F. Schwender, Lebanon; Brooks R. Sunday, Hackettstown, both of N.J.

[73] Assignee: Warner-Lambert Company, Morris Plains, N.J.

[21] Appl. No.: 733,602

[22] Filed: Oct. 18, 1976

Related U.S. Application Data

[63] Continuation-in-part of Ser. No. 614,399, Sep. 18, 1975, Pat. No. 4,012,387.

[51] Int. Cl.$^2$ .................. C07D 471/04; A61K 31/505
[52] U.S. Cl. .......................... 260/256.4 F; 260/251 A; 260/251 QA; 424/251
[58] Field of Search ................................ 260/256.4 F

[56] References Cited

U.S. PATENT DOCUMENTS 3,965,100  6/1976  Yale ............................... 260/256.4 F

OTHER PUBLICATIONS

Halleux, et al., "Chemical Abstracts", vol. 73 (1970), Col. 3874(f).
Fischer, "Chemical Abstracts", vol. 81 (1974), Col. 120573h.

Primary Examiner—Donald G. Daus
Assistant Examiner—James H. Turnipseed
Attorney, Agent, or Firm—Albert H. Graddis; Frank S. Chow; George M. Yahwak

[57] ABSTRACT

Disclosed are novel benzo[g]Pyrido[2,1-b]-quinazolinones which are active as anti-allergy agents and thus have utility in the treatment of allergic reactions such as bronchial asthma.

3 Claims, No Drawings

BENZO[g]PYRIDO[2,1-b]-QUINAZOLINONES

This application is a continuation-in-part of U.S. Patent Application Ser. No. 614,399, filed Sept. 18, 1975, which is now U.S. Pat. No. 4,012,387.

The present invention relates to compounds of the following generic series:

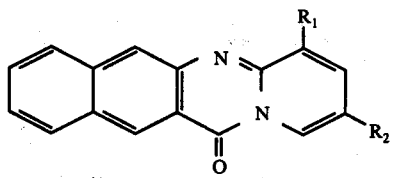

where $R_1$ and $R_2$ are selected from the group consisting of hydrogen, carboxyalkyl, carboxamido, cyano, or 5-tetrazolyl. Alkyl as used above refers to straight or branched chained radicals of 1 to 4 carbons in length. The pharmaceutical salts of these compounds are also within the scope of this invention.

The preferred compounds are those structural species wherein $R_1$ and $R_2$ are hydrogen or 5-tetrazolyl and in which only one tetrazolyl function appears in the generic structure at any one time.

The compounds of this invention may be prepared by the chemical routes in patent application Ser. No. 614,399, the disclosure of which is incorporated herein.

The following examples are given for a more complete understanding of the invention:

EXAMPLE 1

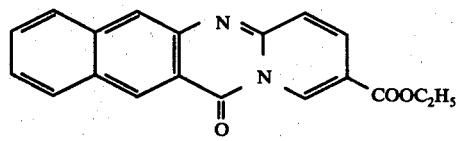

Ethyl 6-oxo-6H-benzo[g]pyrido[2,1-b]quinazoline-3-carboxylate.

A mixture of 3-amino-2-naphthoic acid (30.0 g, 160 mmol), 6-chloronicotinic acid (25.2 g, 160 mmol) and 750 ml of ethanolic hydrogen chloride was heated at reflux for 72 hrs. The reaction mixture was cooled to 0° and the solid collected by filtration to give the hydrochloride salt; 29.6 g, mp 352°-5° dec. The salt was suspended in aqueous ammonia and filtered to give the crude base which yielded the analytically pure ester upon recrystallization from pyridine; yield, 9.1 g (20%), mp 235°-38° dec.

Anal. ($C_{19}H_{14}N_2O_3$) CHN satisfactory.

EXAMPLE 2

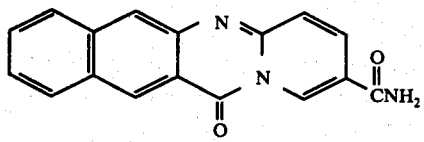

6-Oxo-6H-benzo[g]pyrido[2,1-b]quinazoline-3-carboxamide.

A mixture of 6-chloronicotinamide (16.75 g, 107 mmol), 3-amino-2-naphthoic acid (20.0 g, 107 mmol) and glacial acetic acid (200 ml) was heated at reflux for 24 hrs. The resulting suspension was cooled to room temperature and filtered to give 8.70 g (28.0%) of the crude product, mp 325°-40° dec. One recrystallization from pyridine gave the analytical material, mp 242°-248° dec.

Anal. ($C_{17}H_{11}N_3O_2$) CHN satisfactory.

EXAMPLE 3

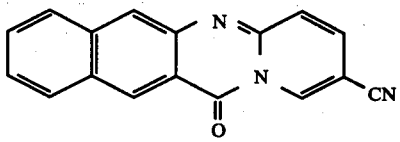

3-Cyano-6-oxo-6H-benzo[g]pyrido[2,1-b]quinazoline.

A reaction mixture containing 3.03 g (10.0 mmol) of 6-oxo-6H-benzo[g]pyrido[2,1-b]quinazoline-3-carboxamide, 2.86 g (15.0 mmol) of p-toluenesulfonyl chloride, 70 ml of DMF and 250 ml of pyridine was heated at 110° for 78 hrs. The resultant orange suspension was cooled and poured onto 1.5 l. ice-$H_2O$ and acidified with conc. HCl. The solid which formed was collected to give 2.60 g (93.2%) of crude nitrile product, mp 355°-58° dec. One recrystallization of the crude nitrile from pyridine gave 2.05 g (73.5%) of the analytically pure nitrile, mp 354°-56° dec.

Anal. ($C_{17}H_9N_3O$) CHN satisfactory.

EXAMPLE 4

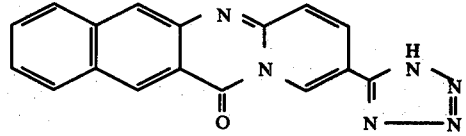

6-Oxo-6H-3-(5-tetrazolyl)-benzo[g]pyrido[2,1-b]quinazoline.

A DMF solution (250 ml) containing 0.68 g (10.5 mmol) NaN$_3$, 0.62 g (10.5 mmol) NH$_4$Cl and 1.0 g (3.68 mmol) of 3-cyano-6-oxo-6H-benzo[g]pyrido[2,1-b]quinazoline was heated at 110° for 32 hrs. The reaction mixture was poured into 1 l. $H_2O$, acidified with conc. HCl and extracted with CHCl$_3$ (2 × 1.5 l.). The combine CHCl$_3$ extracts were dried (MgSO$_4$) and evaporated to give 0.80 g (69.0%) of crude tetrazolyl product; mp 278°-88° dec. One recrystallization of the crude product from pyridine gave the analytical material; yield, 0.40 g (34.5%), mp 295°-302° dec.

Anal. ($C_{17}H_{10}N_6O$) CHN satisfactory.

Compounds of this invention have been found to reduce allergic responses to antigen challenge by inhibiting antibody-antigen reactions in mammals such as rats, when tested in accordance with the procedure of Herzig [Immunopharmacology, M. E. Rosenthale and H. C. Mansmann, Eds., John Wiley and Son, N.Y., 1975]. Following this protocol, the table below shows comparative data between the effectiveness of the compound according to Example 1 and Intal (Chromoglycate) which is presently the commercial compound of choice for use in allergic bronchial asthma.

TABLE I

| | Effective dose 50% inhibition rat passive cutaneous anaphylaxis test ($ED_{50}$-PCA) | | |
|---|---|---|---|
| | $ED_{50}$-PCA(rat) | | |
| | ip. | iv. | po. |
| Example 4 | Active | Active | Active |
| Intal 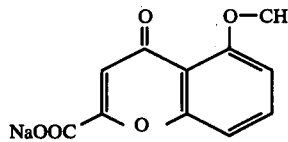 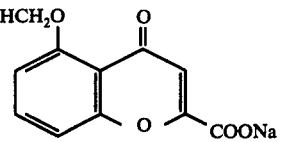 | inactive | Active | inactive |

As can be seen, the Example 4 compound is active when given orally or intraperitonially, whereas the commercial compound is not. Furthermore, when compared for i.v. administration, the novel compound has been found to be ten to fifteen times as effective as the commercial compound.

We claim:

1. A compound of the structure:

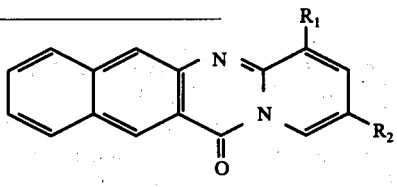

wherein $R_1$ and $R_2$ are selected from the group consisting of hydrogen and tetrazolyl with the proviso that $R_1$ and $R_2$ are not identical and its pharmaceutically acceptable salts.

2. The compound of claim 1 which is 3-(1H-tetrazol-5-yl)-6H-benzo[g]pyrido[2,1-b]-quinazolin-6-one.

3. The compound of claim 1 which is 1-(1H-tetrazol-5-yl)-6H-benzo[g]pyrido[2,1-b]-quinazolin-6-one.

* * * * *